United States Patent [19]

Obenreder

[11] Patent Number: 4,645,337
[45] Date of Patent: Feb. 24, 1987

[54] SYSTEM FOR DETECTING VARIATIONS IN SURFACE COMPOSITION OF AN ARTICLE

[75] Inventor: Robert J. Obenreder, Coraopolis, Pa.
[73] Assignee: PPG Industries, Inc., Pittsburgh, Pa.
[21] Appl. No.: 666,948
[22] Filed: Oct. 31, 1984
[51] Int. Cl.[4] ............................................. G01N 21/55
[52] U.S. Cl. .................................. 356/128; 356/239; 356/445
[58] Field of Search ............... 356/128, 135, 136, 237, 356/239, 431, 445, 448

[56] References Cited

U.S. PATENT DOCUMENTS

| | | | |
|---|---|---|---|
| 2,780,131 | 2/1957 | Lanneau et al. | 356/136 |
| 3,792,930 | 2/1974 | Obenreder | 356/128 |
| 3,857,637 | 12/1974 | Obenreder | 356/371 |
| 3,871,773 | 3/1975 | Shaw | 356/239 |
| 4,536,651 | 8/1985 | Bosse | 356/136 |

*Primary Examiner*—R. A. Rosenberger
*Attorney, Agent, or Firm*—Donald Carl Lepiane; Robert A. Westerlund, Jr.

[57] ABSTRACT

Surface inhomogeneities of a piece of glass are detected by disposing the glass piece in interfacial relation to an optical medium and reflecting light at a predetermined angle of incidence from the glass surface - optical medium interface along a scan path, through at least a portion of the optical medium. The optical medium is selected to have a refractive index equal to the bulk refractive index of the piece of glass. The intensity of the light reflected from the glass along the scan path is monitored to indicate surface inhomogeneities and the location thereof on the glass surface.

6 Claims, 5 Drawing Figures

SYSTEM FOR DETECTING VARIATIONS IN SURFACE COMPOSITION OF AN ARTICLE

1. Field of the Invention

The present invention relates to a system for monitoring the surface characteristics of an article e.g., a piece of flat glass, and more particularly, to a system which is sufficiently sensitive to detect localized surface inhomogeneities of even a minor nature.

2. Discussion of the Technical Problems

In the manufacture of flat glass, batch materials fed into the upstream end of a melter or regenerative furnace are melted in the combustion chamber of the furnace into raw, molten glass as they advance downstream through the melter, and thereafter the raw molten glass is refined. The refined molten glass exits at the downstream end of the furnace, between a tweel and a threshold or lip onto a pool or bath of molten metal. The refined molten glass as it advances downstream on the molten metal pool or molten metal bath forming chamber, is controllably cooled to form a glass ribbon which is lifted from the pool by lift out rolls and moved through an annealing lehr to further refine the glass ribbon.

In the manufacturing process above-described, defects may be produced in the glass which render the glass optically imperfect and/or which diminish the functional qualities or performance of the glass. Among the imperfections that may be produced are surface distortion and index of refraction variations in the glass. "Surface distortion" as used herein refers to variations in surface flatness, i.e., contours in the surface of the glass. "Distortion due to index of refraction variations" as used herein refers to variations in the composition of the glass, such as ream, and defects in the glass, such as bubbles and stones, or to variations in the surface chemistry of the glass, or surface inhomogeneities in the glass. In general, index of refraction variations cause variations in the intensity of the reflected light.

This discussion will be limited to the index of refraction variation type of glass distortion problem, and more particularly, to the index of refraction variations attributable to surface inhomogeneities in the glass, for purposes of aligning the discussion for relevance to the present invention.

It is desirable to detect surface inhomogeneities in glass, as these inhomogeneities can indicate that a problem exists in the manufacturing process. It is even more desirable to detect even minor or slight variations in the surface composition of the glass, as even these slight surface inhomogeneities can produce optical distortion and/or reduce the functional performance or architectural quality of the glass. Further, detection of minor surface inhomogeneities can alert personnel to the existence of manufacturing process problems in their early stages, i.e., before the problems worsen and become more difficult and expensive to solve and/or before too much glass is produced which is unacceptable due to poor quality.

Surface inhomogeneities can be caused by tweel contamination and/or erosion, batch raw materials preparation flaws, imperfect combustion in the melter, improper cooling in either or both the forming chamber or the annealing lehr, or condensate deposits on the glass surface, to name a few causes.

There are presently available techniques and systems for inspecting or monitoring the quality of the glass produced by the above and other processes. These include, among others, the systems taught in U.S. Pat. No. 3,792,930 issued to the present applicant, U.S. Pat. No. 3,871,773 issued to Shaw, Jr., and U.S. Pat. No. 3,857,637 issued to the present applicant. Although these presently available systems facilitate detection of surface contour and/or compositional variations in the glass, these systems are limited insofar as they are not sufficiently discriminatory or sensitive to detect minor or localized variations in the surface composition of the glass. These systems have the further limitation that the specific type of compositional defect is not discernible therewith, e.g., internal glass composition defects cannot be sufficiently distinguished from surface composition defects which, if known, can facilitate indentification and isolation of specific manufacturing process problems. These presently available systems are further limited in that they cannot detect the magnitude and exact location of detected surface inhomogeneities.

SUMMARY OF THE INVENTION

The system of this invention, in one of its aspects, encompasses an apparatus for detecting surface inhomogeneities of a surface of a sample article, e.g., a piece of glass. The apparatus includes an optical medium having a refractive index substantially equivalent to the bulk refractive index of the piece of glass, the optical medium being disposed in interfacial relationship to the piece of glass; means for reflecting a beam of light from the article surface-optical medium interface; means for moving the reflecting light beam means and the glass at a predetermined scanning speed relative to one another along a predetermined scan path; means for detecting the intensity of the reflected light beam along the predetermined scan path, and; means acted on by the light intensity detecting means for indicating surface inhomogeneities on the glass surface as a function of position on the glass surface.

The system of this invention, in another of its aspects, encompasses a method for detecting surface inhomogeneities of a selected surface of a sample article, e.g. a piece of glass. The method includes the steps of directing a beam of light toward the selected glass surface at a predetermined angle of incidence, and reflecting the light beam therefrom, along a predetermined scan path at a predetermined scanning speed relative to the selected glass surface; passing the reflected light beam along the scan path through an optical medium having a refractive index approximately equivalent to the bulk refractive index of the piece of glass; detecting the intensity and determining the position of the reflected light beam relative to the selected surface of the glass piece; and indicating the intensity and position of the reflected light beam along the scan path to monitor surface characteristics of the selected glass surface.

DESCRIPTION OF THE INVENTION

Figure 1:
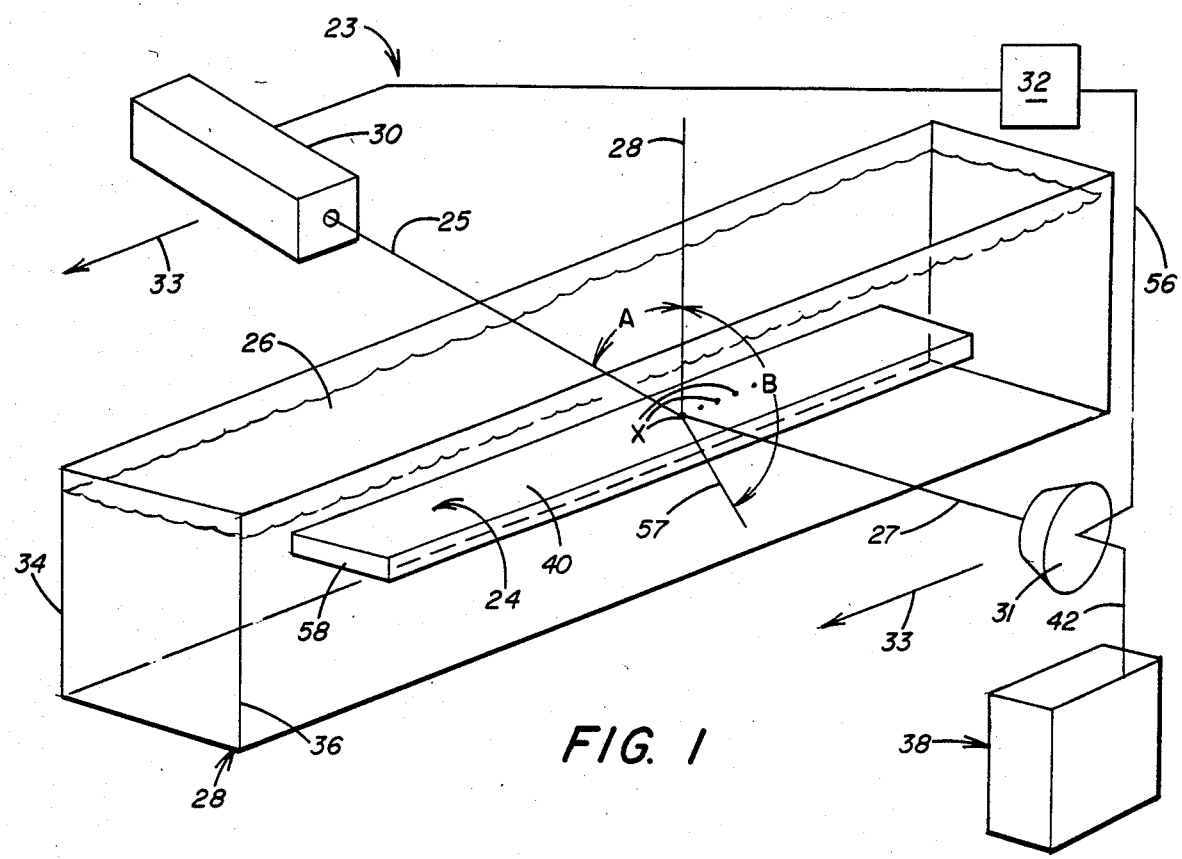
FIG. 1 is a partially perspective, partially schematic representation of a surface composition monitoring system incorporating features of this invention.

Referring to FIG. 1, there can be seen a schematic diagram of a system 22 embodying features of the present invention. The system 22 encompasses an optical medium 26 disposed in interfacial relationship to an article 24 to be monitored by the system 22 for variations in the surface composition of a specular surface thereof, these variations being defined as surface inhomogeneities. In the preferred embodiment of the system 22, the optical medium 26 is a body or pool of refractive index matching oil 26 held by a transparent container 28, e.g., a clear glass (i.e. substantially light-transmissive) container. The optical medium 26, or oil 26, is characterized by a refractive index $N_1$ substantially, preferably exactly, equivalent to the bulk refractive index $N_2$ of the article 24 being monitored. The article 24 can suitably be a piece of clear float glass 24. In the actual practice of the invention, a piece of flat, clear float glass manufactured by PPG Industries, Inc. and having a bulk refractive index $N_2$ of about 1.518 was monitored, and a mineral oil having a refractive index $N_1$ of about 1.518, purchased as specified from Cargille Laboratories, USA, was used as the optical medium 26.

The system 22 further encompasses a light source 30, preferably a continuous wave laser 30, and a light intensity detector 31, preferably a photodetector 31, adapted for synchronous, tandem movement by driving facilities 32 along a predetermined scan path, indicated by the directional arrow 33, at a predetermined, preferably constant, scanning speed relative to the article 24 being monitored, the laser 30 and the photodetector 31 being always disposed, throughout the scan path, in opposed, functional relationship to each other, outside of and along opposite sidewalls 34, 36, respectively, of the container 28. In the actual practice of the invention, the laser 30 employed was a helium-neon laser having a laser beam wavelength of about 6,328 angstroms, and the photodetector 31 employed, was a silicon photovoltaic cell sensitive to laser light incident thereon for detecting the intensity thereof. The driving facilities 32 could, for example, include a motor-driven wormgear (not shown) adapted to reciprocably drive a bridge member (not shown) disposed transversely across the top of the container 28, the bridge member being adapted to carry the laser 30 and the photodetector 31, wherein the motor (not shown) driving the wormgear (not shown) could be pre-set to drive the bridge member at a constant, predetermined speed in a longitudinal direction relative to and above the container 28, whereby the laser 30 and the photodetector 31 would be simultaneously driven along the scan path 33 at a constant, predetermined scanning speed. In actual practice, a synchronous motor (not shown) was used to independently drive the laser 30 and the photodetector 31 along the scan path 33 in synchronicity with each other. Other suitable driving facilities include, among others, linear drive motors, screw drive mechanisms, linear slide mechanisms, trolley and rail mechanisms, rack and pinion mechanisms, and the like. Neither the type of optical medium 26, article 24, light source 30, photodetector 31, nor the type of driving facilities employed in the practice of this invention are limiting thereto. Further, the optical medium 26 and the article 24 could be tandemly moved along the scan path 33 while the laser 30 and the photodetector 31 remain stationarily fixed.

The photocell detector 31 is functionally connected, e.g., via an electrical conduit 42, to a graphical plotter or chart recorder 38, e.g., continuous strip chart recorder, having at least two axes, e.g., an x-axis and a y-axis.

In operation, the system 22 works in the following manner. The laser 30 and the detector 31 are driven by the driving facilities 32 along the scan path 33 at a predetermined, constant scanning speed. The scan path 33 includes a selected portion of the sample surface 40 which is desired to be inspected. For example, and not limiting to the invention, the scan path 33 can be from one end, e.g., 56, to the opposite end, e.g., end 58, of the sample 24, to thereby scan the surface 40 across an entire dimension, e.g. the length thereof.

Figure 2:
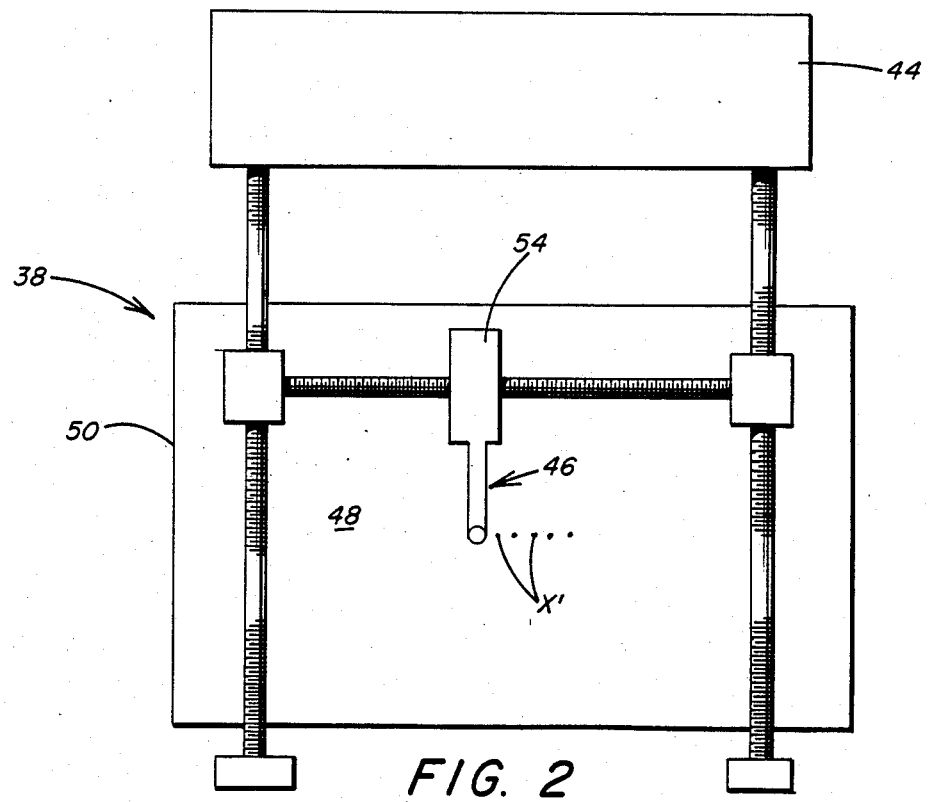
FIG. 2 is a plan, isolation view of a chart recorder which can be used in the practice of this invention.

The laser 30 directs a beam of laser light 25 through the sidewall 34 and the oil 26, the beam 25 then impinging the top surface 40 of the piece of glass 24 (hereinafter termed the glass sample 24) at an angle of incidence A, as measured from a line 28 normal to the top surface 40 of the glass sample 24, at the point of incidence. The top surface 40 should be substantially flat in the direction of the plane of incidence to avoid surface 40 contour variations which vary the angle of incidence A, thereby causing reflectance variations not associated with top surface 40 inhomogeneities. As can be appreciated by those skilled in the art, the surface contour of float glass is essentially flat in the direction in which it is drawn, and it is therefore preferred that this draw direction be oriented parallel to the plane of incidence to avoid confusion between reflectance variations due to contour variations and reflectance variations due to compositional variations of the monitored surface. The angle of incidence A is preferably made to be large, e.g., about 85 degrees, and preferably between 45-90 degrees. The laser light beam 25 is reflected as a reflected laser light beam 27 from the surface 40 of the glass sample 24, and outwardly through the oil 26 and the opposite sidewall 36 of the container 28 and onto the photocell detector 31. Referring additionally to FIG. 2, the reflected light beam 27 energizes the detector 31 to induce a flow of current through the electrical conduit 42 which conveys the current to Y-axis driving mechanism 44 of the chart recording apparatus 38. The strength of the current delivered to the Y-axis driving mechanism 44 is a function of the amount or intensity of the reflected light beam 27 sensed by the photodetector 31. The Y-axis driving mechanism 44 of the chart recorder 38 moves a marking device 46, e.g., a drawing pen, along the y-axis of a recording medium 48, e.g., chart paper, conveniently mounted within holder/-superstructure 50 of the chart recorder 38. The amplitude of movements of the marking device 46 along the y-axis of the recording medium 48 varies proportionally with the amount of current which the driving mechanism 44 receives from the detector 31. As will be hereinafter more fully developed, the intensity of the reflected beam 27 sensed by the detector 31 is a function of the reflectance of the surface 40 being inspected. Therefore, since the magnitude or strength of the current delivered by the detector 31, via the conduit 42, to the Y-axis driving mechanism 44 is a function of the intensity of the reflected light beam 27 sensed by the detector 31, then the strength of the current is also a function of the reflectance of the surface 40 being inspected. Therefore, ultimately, the amplitude of movement of the marking device 46 along the y-axis of the recording medium 48 is also a function of the reflectance of the surface 40.

X-axis driving mechanism 54 of the chart recording apparatus 38 is preset to move the marking device 46 along the x-axis of the recording medium 48, at a constant rate of speed proportional to the predetermined, constant scanning speed of the laser 30 and the detector 31 along the scan path 33. Therefore, the movement of the marking device 46 along the x-axis of the medium 38 is a function of the position of the light beam 25 on the surface 40 of the sample 24 being scanned. More particularly, each point $x^1$ on the medium 38 corresponds to a point x on the surface 40 portion included within the scan path 33, by a known proportion, e.g., in this illustrative case $x^1$ is proportional to x by the same proportion as the proportion of the speed of the device 46 along the x-axis of the medium 48 to the speed of the laser 30 and detector 31, i.e., $x^1/x$=rate of speed of device 46/scanning speed.

The above-discussed operation of the system 22 results in the generation of a graph on the chart paper 48 which plots reflectance R of (or a value which is a function of reflectance) the glass sample surface 40 on the y-axis versus position on the sample surface 40 on the x-axis.

Figure 3:
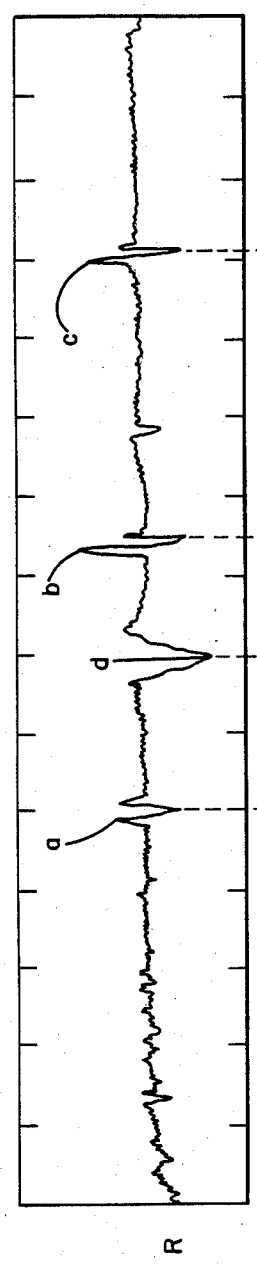
FIG. 3 is an illustrative example of an actual graph produced using the system of this invention.

As can be appreciated, the greater the reflectance, the greater the amplitude of the movement of the marking device 46 along the y-axis and therefore, the greater the amplitude of the resultant graph at the points $x^1$ on the graph paper 48 which correspond to the points x on the surface 40 scanned having the greater reflectance values. This can be clearly seen at the points a, b, anc c on the graph depicted in FIG. 3, which is an illustrative example of an actual graph produced by the system 22, using a 2.3 mm. clear float glass sample 24, which has a bulk refractive index of 1.518. Also, the converse of the above is true, as can be clearly seen at point d. In general, the float glass produced by PPG Industries, Inc. has a bulk refractive index of 1.518 and therefore, the oil 26 selected for use in the system 22 for inspecting or scanning the surface of PPG-produced float glass samples will also generally have a refractive index of 1.518. However, the invention can be practiced with any type of surface sample, the only requirement being that the refractive index of the optical medium 26 be slightly higher than the refractive index of the sample surface. As will hereinafter be more fully developed, when the refractive index of the sample top surface 40 at any point x is equal to the refractive index of the matching oil 26, then the reflectance of the top surface 40 at that point x is zero, and therefore, no reflected laser light beam 27 is received by the photocell detector 31 for that point x, and consequently no current is delivered to the Y-axis driving mechanism 44 of the recording apparatus 38 at the point $x^1$ which corresponds to that point x on the surface 40, and therefore, the amplitude of movement of the marking device 46 is zero at that point $x^1$ and therefore, ultimately, the amplitude of the resultant graph is also zero at that point $x^1$. Otherwise stated, since the amplitude of movement of the marking device 46 along the y-axis is a function of the reflectance of the sample top surface 40, then at any point x on the top surface 40 where the reflectance is zero, the amplitude of movement of the marking device 46 along the y-axis at the point $x^1$ on the chart paper 48 which corresponds to that point x, will also necessarily be zero.

Figure 4:
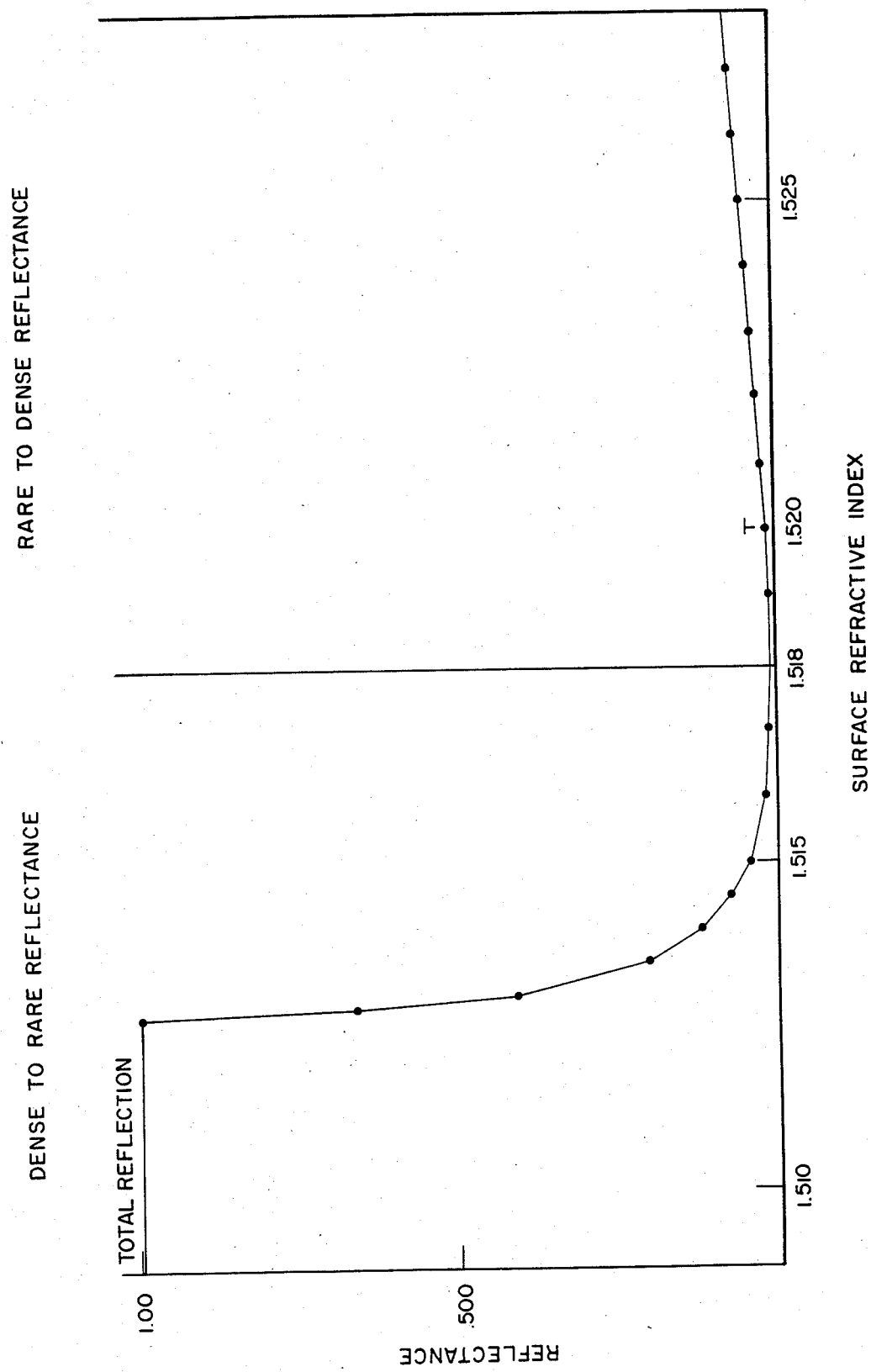
FIG. 4 is a reference graph used in the actual practice of this invention, plotting glass surface reflectance against surface refractive index.

However, if the surface 40 refractive index is either lesser or greater than the refractive index of the matching oil 26, then the surface 40 reflectance will necessarily be greater than zero, and consequently, the amplitude of movement of the marking device 46 will also necessarily be greater than zero, as is evident in FIG. 4. The scientific principles which underly and form the basis for the system 22 of this invention are as follows. The magnitude of the intensity of the light reflected from an interface separating two optical media, namely the glass top surface 40 and the refractive index matching oil 26, can be determined from the relationship, $$R = \frac{1}{2}\left(\frac{\text{Tan}^2(A - B)}{\text{Tan}^2(A + B)} + \frac{\text{Sin}^2(A - B)}{\text{Sin}^2(A + B)}\right),$$ Equation (1)

where A is the angle between the incident laser light beam 25 and the line 28 normal to the interface of the oil 26 and the glass surface 40 and B is the angle between the refracted beam 57 and the interface normal line 28. The relationship between A and B is completely determined by Snell's law, referred to here as equation (2): $N_1 \sin A = N_2 \sin B$, where $N_1$ is the refractive index of the immersion oil 26 surrounding the glass sample 24, and $N_2$ is the refractive index of the glass top surface 40. In the actual practice of the invention, the oil 26 selected had a refractive index $N_1$ of 1.518, which is essentially equivalent to the bulk refractive index of float glass manufactured by PPG Industries, Inc. The angle A of the incident light beam 25 was about 85 degrees, to maximize the sensitivity of the system 22 to localized surface compositional variations, as will hereinafter be more fully developed and appreciated. FIG. 4 is a graph plotting the interface reflectance values R yielded by the equation (1) for an 85 degree light beam 25 angle of incidence over a range of values of glass top surface 40 refractive index $N_2$ both higher and lower than the 1.518 value for $N_1$. Whenever $N_1 = N_2$, it can be appreciated from the equation (2) that regardless of the magnitude of the angle of incidence A, the angle of refraction B will be exactly equal to it, and the numerators in both terms of equation (1) will therefore be zero. Thus, when the glass top surface 40 refractive index $N_2$ equals the refractive index $N_1$ of the oil 26, the reflectance R will be zero. However, when $N_2$ is greater than $N_1$, the reflectance R is substantially a linear function of the top surface 40 refractive index $N_2$ at a given angle of incidence A, e.g. 85 degrees. When $N_2$ is greater than $N_1$, this is termed "rare to dense" or external reflectance, wherein minor variations in the glass top surface 40 refractive index $N_2$ result in generally minor variations in the glass top surface 40 reflectance R. Conversely, it can be seen in FIG. 4 that when $N_2$ is less than $N_1$, the reflectance R is a non-linear function of the glass top surface 40 refractive index $N_2$, at large angles of incidence A, e.g., 85 degrees. When $N_2$ is less than $N_1$, this is termed "dense to rare" or internal reflectance, wherein, depending on the angle of incidence A selected, minor variations in the glass top surface 40 refractive index $N_2$ can result in major or great variations in the reflectance R. In the usual case, the glass top surface 40 will generally have a lower refractive index $N_2$ than the bulk refractive index of the entire glass sample 24, due to the fact that the top surface of float glass tends to be silica-rich and silica has a lower refractive index than the bulk of the glass. Therefore, when the refractive index $N_1$ of the index matching oil 26 is selected to be roughly equivalent to the bulk refractive index of the glass sample 24 under inspection, the situation is one of "dense to rare" or internal reflectance, wherein slight variations in the glass top surface 40 refractive index $N_2$ result in great variations in the surface reflectance R, at a high angle of incidence, e.g., 85 degrees.

The information generated by the system 22 of this invention in the form of a graph on a recording medium such as chart-paper 48, can be acted on to determine the magnitude and location of surface 40 defects. Deviations in the refractive index $N_2$ of the sample surface 40 as signified by varying reflectance R of the surface 40 on the chart paper 48 graph, correspond to variations in the surface composition of the sample surface 40, these surface variations being defined as surface inhomogeneities. Surface inhomogeneities can be caused by problems or deficiencies in the glass making process, and more particularly, can be attributable to defects in the various stages of the glass making process, such as in batch raw materials preparation, melting, refining, forming, or annealing. In order to use the graphical information generated by the system 22 of the this invention to remedy or correct a process problem, especially before the problem becomes greater and/or more difficult and expensive to solve, it is necessary to analyze what points or areas on the glass sample surface 40 exhibit varying reflectance, which is indicative of surface inhomogeneity. For example, if the tweel (not shown) becomes locally contaminated and/or erodes, it has a tendency to transfer or deposit silica onto the surface of the molten glass as it exits the melting furnace and enters the molten metal forming bath chamber. A portion of the surface 40 which has been silica-enriched in this manner exhibits a lower refractive index $N_2$ due to the fact that silica has a refractive index lower than the bulk glass refractive index. Further, since reflectance R varies greatly with minor variations of surface refractive index $N_2$ less than the refractive index $N_1$ of the matching oil 26, i.e., case of "dense to rare" reflectance, (see FIG. 4), the chart paper 48 graph will indicate these variations very clearly as large variations in the amplitude of the graph along the y-axis at the points $x^1$ which correspond to the silica-rich points x on the dimension of the glass sample surface 40 scanned. Thus, a glass surface 40 compositional uniformity scanning or monitoring system 22 incorporating the "dense to rare" or internal reflectance parameters will achieve great sensitivity to surface inhomogeneities. With the scanning system 22 made in accordance with this invention, surface reflectance R variations were easily detected with glass top surface 40 silica variations on the order of approximately 0.1 percent, which corresponds to glass top surface 40 refractive index $N_2$ variations of 0.0003.

A method for determining whether or not surface inhomogeneities are attributable to tweel contamination and/or erosion is to selectively cut several ribbon-wide sections or samples 24 from the glass ribbon or from glass sheets cut from the glass ribbon before their surfaces are treated, e.g., treated with powder interleaving, or after cleaning their surfaces. The samples 24 thus taken are inspected for surface inhomogeneities by the system 22 of this invention in the above-described manner. If the surface inhomogeneities appear at substantially the same location(s) on the various sample surfaces 40 inspected, then the problem is probably due to a tweel defect, and the tweel should be inspected for a determination of the nature of its defect, if any. Preferably, samples 24 are taken from the float glass production line (not shown) at regular intervals so that any process problems can be detected before very much defective glass, which may have to be discarded, is produced and/or before the problem worsens and becomes more difficult to solve.

Although the above-discussed tweel problem is representative of the types of manufacturing process problems which can cause surface chemistry variations or inhomogeneities, this type of problem is merely illustrative of process problems which can occur. Other representative process problems include, but are not limited to, incomplete or excessive combustion in the combustion chamber of the melting furnace, condensation and precipitation in the float bath, annealing lehr, etc.

The present invention further encompasses the preparation or compilation of a database which correlates specific reflectance R variations with specific types of surface 40 chemistry variations, or inhomogeneities. More particularly, the surface 40 refractive index $N_2$ has a known, fixed/established relationship with surface 40 reflectance R and even more particularly, the relationship graphically illustrated in FIG. 4 exists when the refractive index $N_1$ of the index matching oil 26 is 1.518, and the laser light beam 25 angle of incidence A is set to be 85 degrees. From this fixed relationship, the surface 40 refractive index $N_2$ can be determined when the reflectance R is known. The reflectance R is related to the amplitude of the chart paper 48 graph by a known proportion (e.g. 1/1, or ½, etc.). In other words, the reflectance R of a glass sample surface 40 inspected with the system 22 of this invention, assuming all of the system 22 parameters are preset as delineated above, can be determined for every point x along the dimension of the sample 24 scanned, by mere interpretation of the chart paper 48 graph generated. Then, by mere reference to the reference graph of FIG. 4 the surface 40 refractive index $N_2$ can easily be determined for every point x along the dimension, e.g., the width, of the sample 24 scanned. Various techniques can then be employed to chemically analyze the surface 40 at the locations wherein it has been determined that surface inhomogeneity exists. Representative of these analytical techniques are x-ray fluorescence, electron microprobe analysis, titration, striaegrammetry, and spectroscopic analysis. The information or database thus generated can be manipulated and recorded in such a manner as to correlate reflectance with surface, chemical composition. This resultant database can then be employed as a reference tool in conjunction with the system 22 of this invention to monitor the manufacturing process. Various types of surface inhomogeneities indicate particular types of manufacturing process shortcomings or deficiencies, which can be corrected or remedied accordingly.

Figure 5:
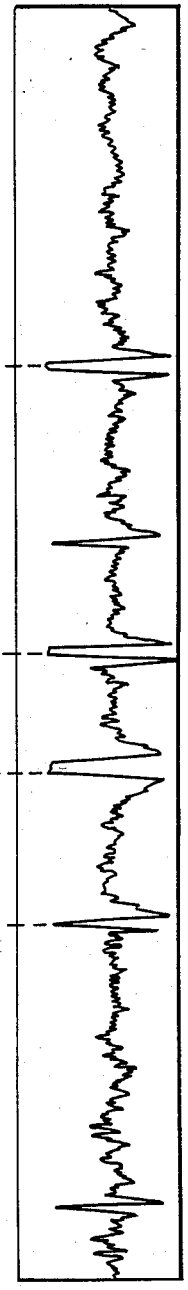
FIG. 5 is a graph which depicts transmitted distortion versus position on the bottom surface of the glass sample used in the generation of the graph of FIG. 3.

Furthermore, top surface inhomogeneity is strongly correlated with bottom surface optical distortion of the glass. More particularly, reference being made to FIG. 5 a device taught in U.S. Pat. No. 3,792,390, issued to the present applicant and assigned to the present assignee, which teachings are herein incorporated by reference, was employed to examine several glass samples, which were determined with the system 22 to exhibit top surface inhomogeneity for bottom surface optical distortion, and the graph in FIG. 5 was generated therewith. The high amplitude portions of the graph shown in FIG. 5 positively indicates severe distortion on the bottom surface of the sample 24 used in the production of the graph of FIG. 3 using the system 22 of this invention. The x-axis of the graph of FIG. 5 and the x-axis of the graph of FIG. 3 correspond substantially exactly. It can be seen that the severe distortion on the bottom surface corresponds substantially exactly with the surface inhomogeneities of the top surface, by way of comparison of the graphs of FIG. 5 with the graph of FIG. 3. Moreover, there seems to be a tendency for a greater-than-average top surface reflectance, indicating increased silica, to be associated with negative optical power on the bottom surface. Conversely, there also seems to be a tendency for a lower-than-average top surface reflectance, indicating either a localized lessening of silica enrichment or an enrichment of CaO or some other high refractive index component to be associated with positive optical power on the bottom surface of the glass. Other optical analytical techniques have been employed to confirm this relationship. These techniques include surface etching, optical flat techniques, and shadowgraph techniques, among others, as are shown to be skilled in the pertinent art.

What is claimed is:

1. A method of detecting changes in the surface composition of an article wherein the surface of the article reflects light and the changes in the surface composition alters the index of refraction of the surface, comprising the steps of:

contacting the surface of the article with a fluid medium having a refractive index substantially equal to bulk refractive index of the an article;

directing a beam of light through the medium onto the surface of an angle of incidence greater than zero to reflect a beam of light from the surface through the medium as a reflected beam of light; and monitoring intensity of the reflected beam of light to delete changes in the surface composition of the article.

2. The method as set forth in claim 1 wherein it further includes the step of imparting relative movement between the article and the directed beam of light to establish a scan path and said monitoring step includes measuring the intensity of the reflected light along the scan path.

3. The method as set forth in claim 2 wherein said monitoring step includes recording information as a function of the intensity of the reflected beam of light and as a function of position on the scan path.

4. The method as set forth in claim 3 wherein the article is a glass article and the angle of incidence is between about 45° and about 90°.

5. The method as set forth in claim 4 wherein the fluid medium is oil having a refractive index of about 1.518 and the glass article has a bulk refractive index of about 1.518.

6. The method as set forth in claim 5 wherein the glass article is cut from a glass ribbon produced by a glass manufacturing process, and further including the step of making corrective adjustments to the glass manufacturing process in response to said recording step.

* * * * *